United States Patent [19]
Cockburn

[11] Patent Number: 6,053,871
[45] Date of Patent: Apr. 25, 2000

[54] CALIBRATED HOLLOW PROBE FOR USE WITH ULTRASOUND IMAGING

[75] Inventor: John F. Cockburn, Jersey, United Kingdom

[73] Assignee: William Cook Australia Pty. Ltd, Australia

[21] Appl. No.: 09/007,925

[22] Filed: Jan. 16, 1998

[51] Int. Cl.[7] .................................................. A61B 8/12
[52] U.S. Cl. ............................................ 600/459; 600/461
[58] Field of Search .................................... 600/461, 464, 600/471; 604/22; 601/2–4; 606/159, 169

[56] References Cited

U.S. PATENT DOCUMENTS

| | | | |
|---|---|---|---|
| 3,556,079 | 1/1971 | Omizo | 600/461 |
| 4,401,949 | 8/1983 | Gold | 324/402 |
| 4,768,496 | 9/1988 | Kreizman et al. | 604/22 |
| 4,811,740 | 3/1989 | Ikeda et al. | 600/459 |
| 4,959,049 | 9/1990 | Smirmaul | 604/22 |
| 5,081,993 | 1/1992 | Kitney et al. | 128/916 X |
| 5,095,910 | 3/1992 | Powers | 600/461 |
| 5,209,235 | 5/1993 | Brisken et al. | 600/463 |
| 5,383,874 | 1/1995 | Jackson et al. | 606/1 |
| 5,391,144 | 2/1995 | Sakurai et al. | 604/22 |
| 5,413,573 | 5/1995 | Koivukangas | 606/1 |
| 5,505,693 | 4/1996 | Mackool | 604/22 |
| 5,517,994 | 5/1996 | Burke et al. | 600/437 |
| 5,544,660 | 8/1996 | Crowley | 600/463 |
| 5,549,112 | 8/1996 | Cockburn et al. | 600/461 |

*Primary Examiner*—Francis J. Jaworski
*Attorney, Agent, or Firm*—Richard J. Godlewski

[57] ABSTRACT

A medical device which has a connection between a signal generating device and a hollow probe, the connection providing a smooth air conduit from the signal generating device to the hollow probe. The medical apparatus includes the probe having a characteristic which is useful to assist with the positioning of the probe in a human or animal body, and an information encoding component on the probe, a selected value of the information encoding component being corresponding to the characteristic of the probe. An interrogating device interrogates the information encoding device.

33 Claims, 4 Drawing Sheets

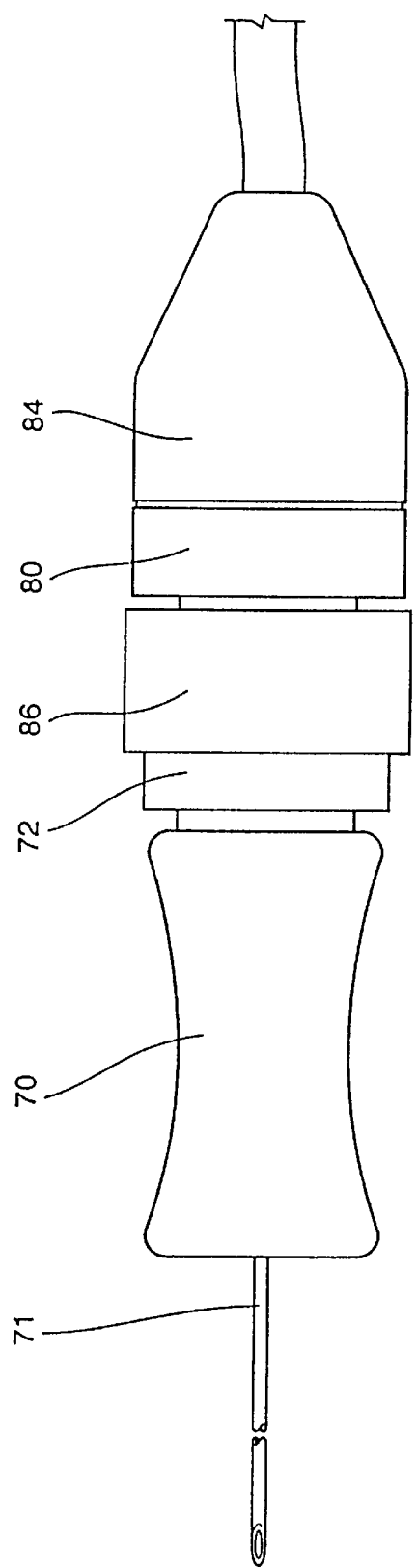
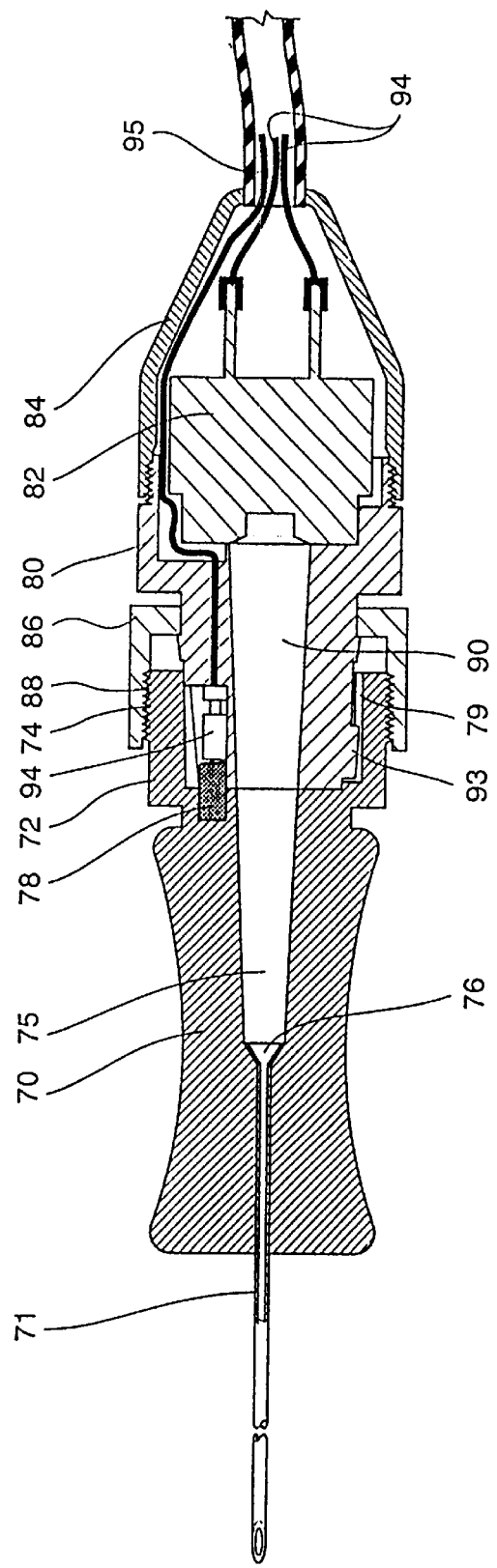
FIG. 7
FIG. 8

CALIBRATED HOLLOW PROBE FOR USE WITH ULTRASOUND IMAGING

RELATED APPLICATIONS

This application claims priority of Australian provisional application No. PO4689, filed Jan. 21, 1997.

TECHNICAL FIELD

This invention relates in general to a medical apparatus and in particular to probes such as hollow probes used for medical procedures and the ultrasonic imaging of such probes.

BACKGROUND OF THE INVENTION

The accurate localization of hollow probes, such as needles and catheters, by ultrasound, particularly those needles and catheters used in diagnostic and surgical procedures, is described in several articles (for example, Ultrasonics, 1988, vol. 26, pp 27–30; Journal of Ultrasound in Medicine, 1990, vol. 9, pp 243–245; and Medical Electronics, April, 1995, pp 64–65) and in several patents (for example, EP A 0083973; EP A 0453251 U.S. Pat. No. 5,095,910; GB A 2157828). This technology arose from the need for fast, accurate location of the tips of needles and catheters. For example, in aspiration biopsy, it is important that the tip of the biopsy needle be accurately placed into the area of interest before a tissue sample is collected.

A disclosure relating to a method for enhancing the visibility of a hollow probe to a Doppler ultrasound imager is described in U.S. Pat. No. 5,549,112. This disclosure provides an apparatus comprising a hollow tubular probe, such as a needle, which is adapted for insertion into body tissue, the hollow probe being provided with a transducer which is substantially mechanically isolated from the probe and coupled to a fluid column within the probe, the transducer being arranged to generate a longitudinal oscillation of said fluid column at a sub-ultrasonic frequency which enhances the visibility of the probe tip to Doppler ultrasound imaging. One means by which the transducer might be mechanically isolated from the hollow probe is to couple the transducer to a column of air or gas in a flexible connecting tube, the internal lumen of which communicates with the bore of the probe.

One problem with the disclosure described in U.S. Pat. No. 5,549,112 is that the optimal visualization of the tip of hollow probes of different lengths and diameters may require the generation of longitudinal oscillation of different frequencies and/or amplitudes. The colour of a region of a Doppler ultrasound image is dependent on the velocity of the corresponding region of tissue and this velocity will vary with the frequency and amplitude of the oscillation of the end of the fluid column at the probe tip. In turn, the frequency and amplitude are dependent on both the mechanical properties of the tissue being vibrated by the fluid column and on the mechanical properties of the connecting tube and/or the probe itself.

Accordingly, it may be necessary for the user of such a device to adjust, recalibrate or reprogram the frequency delivered by the transducer each time that a probe system, consisting of a connecting tube and probe, with a different length and/or diameter and/or material is utilized.

OBJECT OF THE INVENTION

One object of the current invention is to provide for efficient transfer of oscillation signals to the hollow probe.

Another object of the current invention is to provide for an efficient and safe mechanism to automatically select the most appropriate frequency, generated by devices such as those described above, for optimal visualization the tip of a particular hollow probe, such as the tip of a biopsy needle, to Doppler ultrasound imaging.

The invention may not only replace a tedious manual adjustment but also reduces the risks of errors associated with such manual processes, such as incorrect adjustment, fatigue, and lack of concentration.

SUMMARY OF THE INVENTION

In one form the invention may be said to reside in a medical apparatus including a probe, the probe having a characteristic which is useful to assist with the positioning of the probe in a human or animal body, and an information encoding component on the probe, a selected value of the information encoding component corresponding to the characteristic of the probe.

Preferably the probe is a hollow probe.

The characteristic may be a resonant frequency of the probe which enhances the visibility of the tip of the probe to Doppler ultrasound imaging.

The information encoding component may be selected from the group which comprises an electrical resistor, a capacitor and a programmable device. The programmable device, may be for example a non-volatile memory device, such as a RAM or ROM. Alternatively, the programmable device might be a PROM, EPROM or $E^2$PROM.

The probe may comprise a hollow tube and a connector at one end thereof and the information encoding component may be associated with the connector.

The medical apparatus may further comprise a signal generating device for the probe and an interrogating means associated with the frequency generating device to interrogate the information encoding component.

The probe may be a dual lumen needle comprising an inner needle and an outer needle and the distal and of the inner needle may have a closed end and a side hole.

Preferably, the generating device provides an acoustic signal.

In an alternative form the invention may be said to reside in a medical apparatus comprising a hollow probe, a signal generating device and a connecting tube between the hollow probe and the signal generating device, a first connector between the signal generating device and the connecting tube, the first connector including a first portion associated with the signal generating device and a second portion associated with the connecting tube, an information encoding component associated with the second portion and an interrogating means associated with the first portion wherein when the first and second portions of the first connector are connected the interrogating means engages and is able to interrogate the information encoding component.

Preferably the first connector provides a smooth air conduit between the signal generating device and the bore of the connecting tube.

The apparatus may further comprise a second connector between the connecting tube and the hollow probe.

The hollow probe may be a dual lumen needle comprising an inner needle and an outer needle.

Preferably the second connector provides a smooth air conduit between the bore of the connecting tube and the bore of the inner needle.

The second connector may include means to enable disconnection of the coupling tube from the outer needle and removal of the coupling tube and inner needle while leaving the outer tube insitu.

The distal end of the inner needle may have a closed end and a side hole.

In an alternative form the invention may be said to reside in a medical apparatus comprising a hollow probe and a signal generating device and a connector between the signal generating device and the hollow probe, the connector comprising a first portion associated with the signal generating device and a second portion associated with the hollow probe, an information encoding component associated with the second portion and interrogating means associated with the first portion, wherein when the first and second portions of the connector are connected the interrogating means engages the information encoding component.

Preferably the connector provides a smooth air conduit between the signal generating device and the bore of the hollow probe.

In an alternative form the invention may be said to reside in a medical apparatus comprising a signal generating device in a housing and a hollow probe, the hollow probe having a hub at one end thereof and an aperture through the hub providing a fluid passage into the hollow probe, a connection assembly between the housing and the hub, a signal port in the housing extending from the signal generating device to the aperture in the hub, characterized by a smooth fluid conduit extending from the signal port through the aperture to the hollow probe.

Preferably the aperture is tapered to connect with a Luer fitting.

The hub may have an information encoding component and the housing have an interrogating component wherein the connection of the hub to the housing by means of the connection assembly enables the interrogating component to engage the information encoding component.

In an alternative form the invention may be said to reside in a medical apparatus comprising a hollow probe and a signal generating device and a connection assembly between a signal generating device and the hollow probe, the hollow probe having a first bore and the signal generating device having a signal port having a second bore, the connection assembly including a first portion associated with the signal generating device and a second portion associated with the hollow probe and a hub associated either the first portion or the second portion, the hub including an aperture providing a smooth transition between the first bore and the second bore.

Preferably the aperture is of frustoconical shape having a diameter at one end equivalent to the diameter of the first bore and the diameter at its other end equivalent to the diameter of the second bore.

The medical apparatus may further include the hollow probe having an information encoding component and the signal generating device having an interrogating component wherein connection of the hollow probe to the signal generating device by means of the connection assembly enables the interrogating means to engage the information encoding component.

In an alternative form the invention may be said to reside in a connection between a signal generating device and a hollow probe, the connection providing a smooth air conduit from the signal generating device to the hollow probe for the transmission of acoustic signals therethrough.

Preferably the connection includes a tapered portion associated with the hollow probe to enable connection thereto of a Luer fitting.

Further the connection may include an information encoding component associated with the probe and an interrogating component associated with the signal generating device and making the connection enables the interrogating means to engage the information encoding component.

The medical apparatus according to the various embodiments of this invention may further including an electronic control circuit adapted to interrogate the information encoding component and to adjust the frequency of the signal provided by the signal generating means in response to the interrogation.

Hence it will be seen that according to one aspect of the invention there is provided a hollow probe which includes an information encoding component, a known characteristic of which is selected to correspond to those characteristics of the probe that are important for optimal localization of the probe tip by Doppler ultrasound imaging.

According to another aspect, the invention provides a smooth transition from the signal generating device to the hollow probe for efficient transfer of the signal to the tip of the probe.

BRIEF DESCRIPTION OF THE DRAWING

This then generally describes the invention but to assist with understanding the invention will now be described with reference to particular preferred embodiments of the invention by way of example with reference to accompanying drawings wherein:

FIG. 7 shows an alternative embodiment of the medical apparatus of the present invention comprising a hollow probe and the signal generating device, FIG. 8 shows a section view of the embodiment shown in FIG. 7.

DETAILED DESCRIPTION

Figure 1:
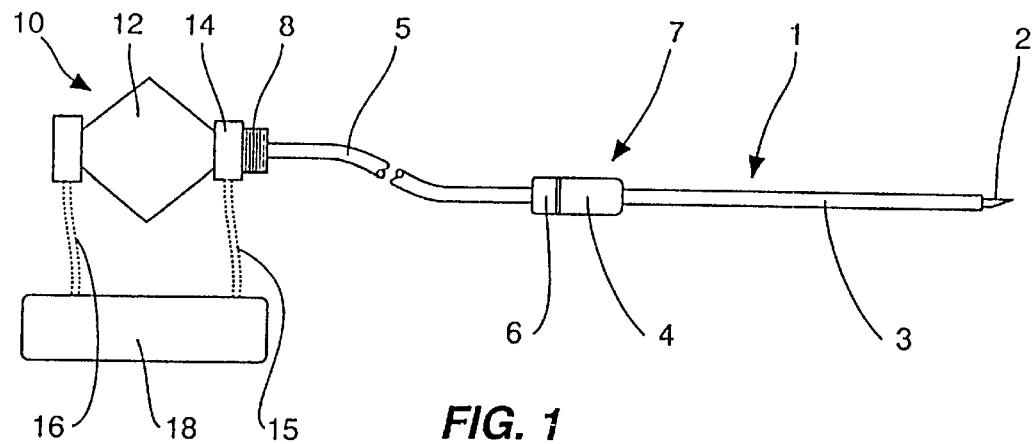
FIG. 1 shows a schematic representative diagram of one embodiment of the medical apparatus comprising a hollow probe and the signal generating device.

FIG. 1 shows one embodiment of medical apparatus having a hollow probe 1, a flexible connecting tube 5 and a signal generating device 10. The hollow probe 1 consists of an inner needle 2 and an outer needle 3 and a connection portion 4. The attached connecting tube 5 has a connection portion 6 which together with the connection portion 4 forms a connection coupling 7. The bore of the inner needle 2 is continuous with the inner lumen of the attached connecting tube 5. The other end of the connecting tube 5 has a connection assembly 8 that allows it to be coupled to the signal generating device 10.

The signal generation device 10 has a housing 12 which contains an acoustic signal generator, a connection portion 14 that allows it to be fitted to the connection tube 5 by means of the connection assembly 8 and electrical wires 15 and 16 which connect the signal generating device 10 to an electronic control circuit 18. The electronic control circuit 18 is connected to the interrogation assembly within the connection portion 14 by the wire 15 and this reads the information encoding component within the connection assembly 8 and hence provides frequency control for the signal generating device 10 to give an optimum frequency acoustic signal transmitted down the hollow probe.

Figure 2:
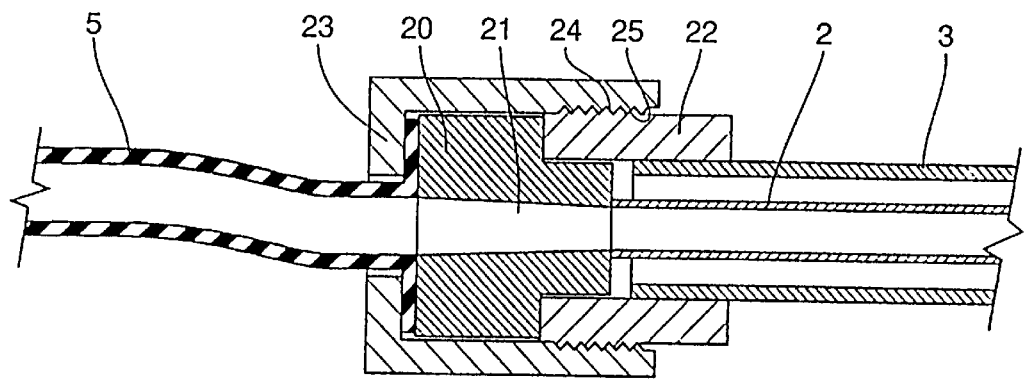
FIG. 2 shows a schematic representation of one embodiment of a coupling between the flexible connecting tube and the needle that is part of the probe.

FIG. 2 shows the preferred embodiment of the coupling 7 of the hollow probe 1 to the connecting tube 5. This coupling is constructed in such a way that the inner needle 2 and the connecting tube 5 can be uncoupled and withdrawn from the outer needle 3. This leaves the outer needle 3 insitu for various medical procedures such as aspiration or sample collection or accurate placement of pharmaceuticals. The inner needle 2 and the connecting tube 5 are joined by a fitting 20. The inner lumen 21 of the joining fitting 20 is formed in such a way that there is a smooth transition, free from perpendicular surfaces, from the inner walls of the connecting tube 5 to the inner needle 2. By this means there is minimal loss or distortion of the acoustic signal. The fitting 20 is coupled to the hub 22 on the outer needle 3 by means of a rotating locking ring 23 which locks to the hub 21 by means of a mating threads 24 and 25 on the two components respectively.

Figure 3:
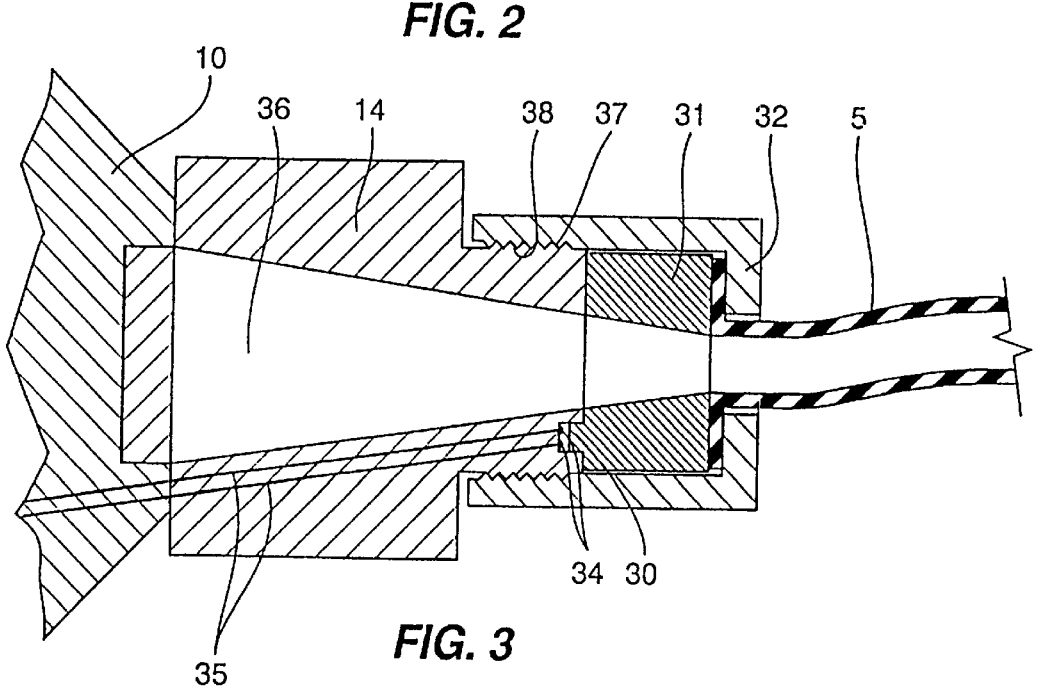
FIG. 3 shows a schematic representation of one embodiment of a coupling of the distal end of a flexible connecting tube, being that part of the probe containing the encoding component, to the signal generating device, FIG. 4 show a schematic representation of one embodiment of the contact between the information encoding component and the interrogating means of the signal generating device.

FIG. 3 shows a preferred embodiment of the coupling of connecting portion 8 on the connecting tube 5 and connection portion 14 on the signal generating device housing 12. This coupling is constructed in such a way an information encoding device 30, situated on a hub 31 at the end of the connecting tube 5 of the hollow probe, makes contact with an interrogating means 34 situated on connection portion fitting 14 on the signal generating device. The interrogating means 34 transmits appropriate information from the encoding component 30 to an electronic control circuit 18 (refer FIG. 1) via electrical wires 35. The inner lumen 36 of fitting 14 is formed in such a way that there is a smooth transition, free of perpendicular surfaces, of the walls of the inner lumen 36 from the signal generating device 10 to the connecting tube 5 through the hub 31. By this means there is minimal loss or distortion of the acoustic signal. The hub 31 is coupled to fitting 14 by means of a rotating locking ring 32 which locks to fitting 14 by means of mating threads means 37 and 38 on the two components respectively.

Figure 4:
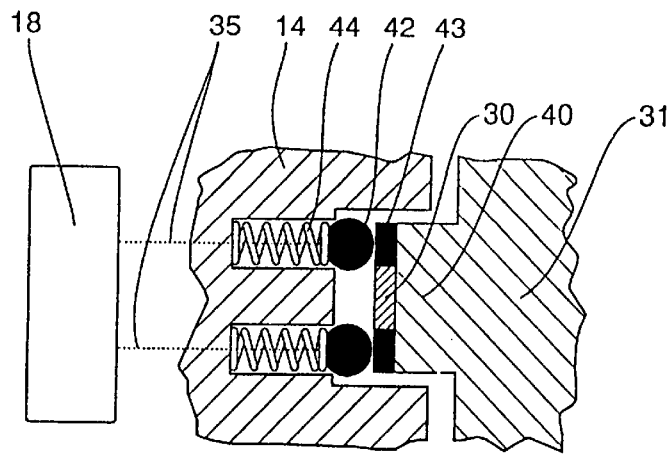

FIG. 4 shows detail of one embodiment of the information encoding component 30 on hub 31 which is part of the fitting 8 (refer FIG. 1) at the proximal end of the hollow probe 1, and the interrogating means 34 on fitting 14 of the frequency generating device 10 (refer FIG. 1). The information encoding component 30, for example a surface-mount resistor of known value, is situated on the end of a post 40 on hub 31. The interrogating means 34 consists of two metal contacts 42 each supported by a spring 44. When the hub 31 is coupled to fitting 14 the metal contacts 43 on the information encoding component 30 make contact with the metal contacts 42 of the interrogating means 34 which transmits appropriate information from the encoding component 30 to an electronic control circuit 18 (refer FIG. 1) via electrical wires 35.

Figure 5:
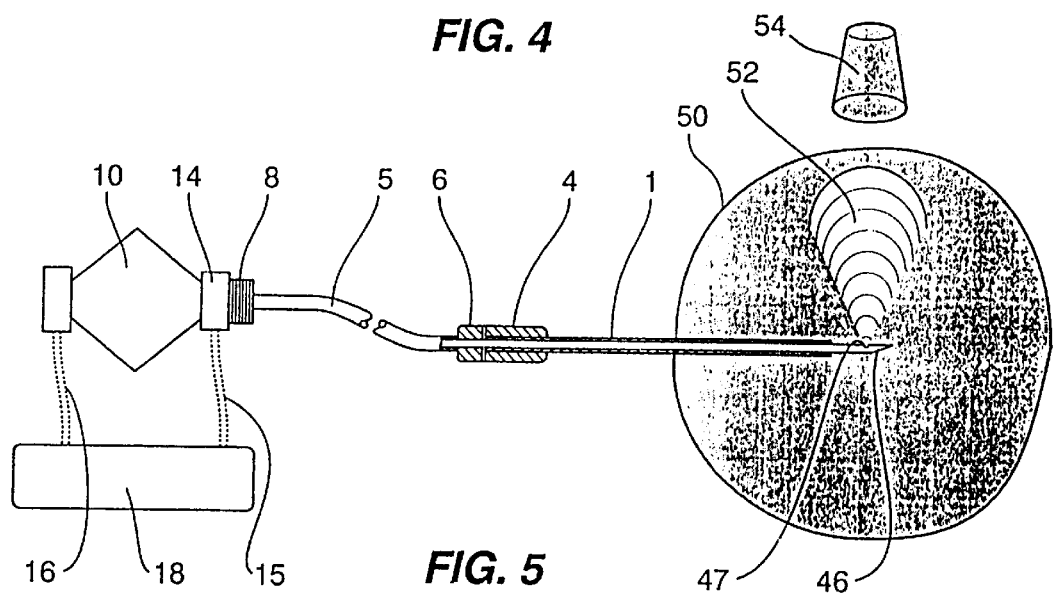
FIG. 5 shows a schematic representation of the use of one embodiment of the medical apparatus comprising a probe and the signal generating device.

One example of the use of this embodiment of the invention will now be described with reference to FIGS. 4 and 5.

The selected hollow probe 1 has at the distal end of the inner needle 2 a closed end 46 and a side hole 47. Fitting 8, at the end of the probe system, is attached to fitting 14 on the signal generating device 10. The interrogating means 34 in fitting 14 transmits appropriate information from the information encoding component 30 in fitting 8 to an electronic control circuit 18 via the electrical wire 15. The electronic control circuit 18 subsequently controls the signal generating device 10, via an electrical wire 16, such that the signal generating device 10 generates the appropriate frequency and amplitude for the selected probe, as coded by the information encoding component 30.

The needle assembly of inner needle 2 and outer needle 3 on the hollow probe 1 is inserted into the tissue 50 from which a biopsy is to be taken. As it is inserted, the signal generating device 10 generates a longitudinal oscillation of the air column at a sub-ultrasonic frequency, within the connecting tube 5 and the inner needle 2, which induces an oscillation 52 of the tissue near the tip of the needle around the side hole 47, enhancing the visibility of the needle tip to Doppler ultrasound imaging from an imaging device 54.

When the tip of the needle is situated in the appropriate position within the tissue, the inner needle 2 is withdrawn from the outer needle 3, without disturbing the position of the outer needle 3, and suction is applied to the hub 22 at the end of the outer needle 3, in order to collect tissue or liquids for biopsy.

It should be appreciated that the scope of the present invention is not limited to the example described above where it is used to locate the tip of a biopsy needle but also relates to the localization of the tip of any hollow probe for any reason.

Figure 6:
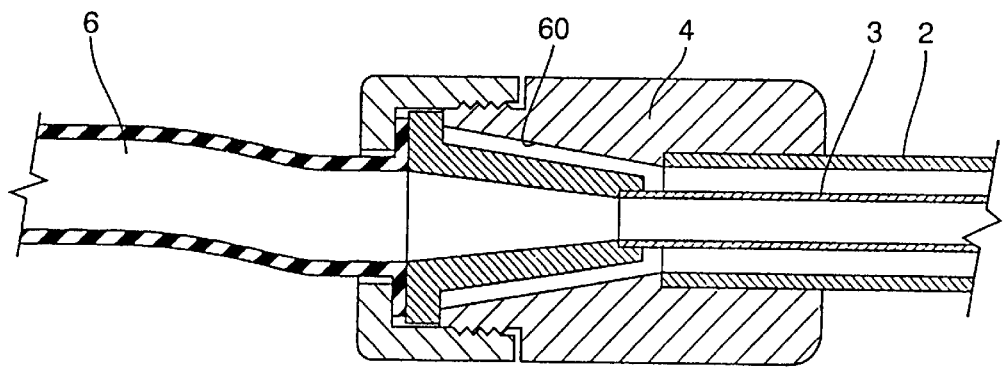
FIG. 6 shows an alternative embodiment of a coupling between the flexible connecting tube and the needle that is part of the probe.

FIG. 6 shows an alternative embodiment of the connection assembly 7 between the needle assembly of the inner needle 2 and outer needle 3 and the connecting tube 5. It should be noted, however, that a similar connection system could be used where the needle assembly of the inner needle 2 and outer needle 3 is connected directly to the signal generating means without the use of the connection tube 5.

In this embodiment the connecting portion 4 has an inner lumen 60 which is of a frustoconical shape which is the same taper as standard Luer connection used in medical technology. This allows the direct connection of the outer needle to a syringe or vacuum extraction device after positioning and removal of the inner needle 2.

It may be noted, too, that an inner needle need not be used in all cases with either the connecting tube 5 or the signal generating means connecting directly to the outer needle 3.

Figure 9:
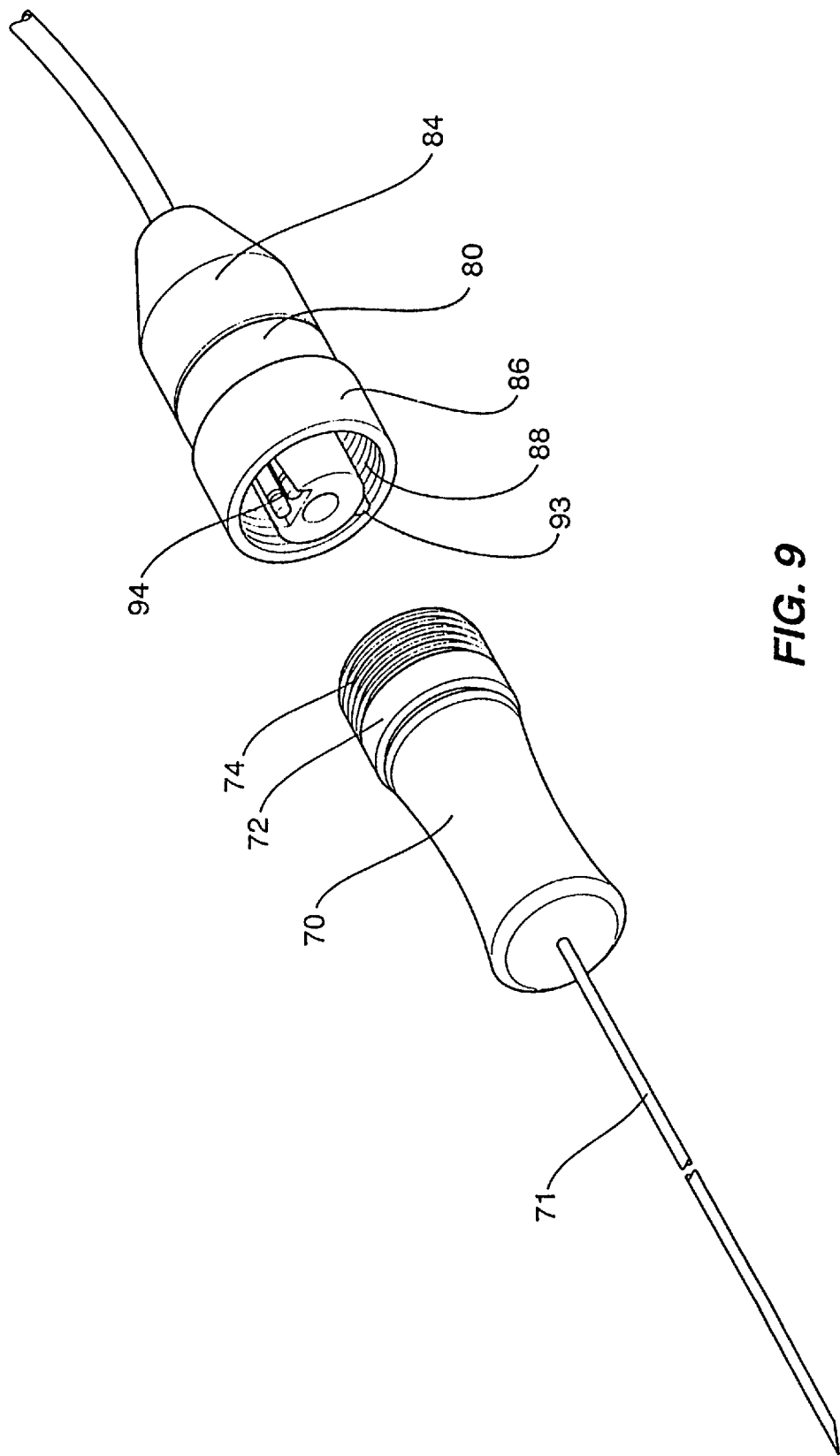
FIG. 9 shows a disassembled view of the medical apparatus shown in FIG. 7.

FIGS. 7, 8 and 9 show an alternative embodiment of the medical apparatus of the present invention comprising a hollow probe and a signal generating device.

The medical apparatus comprises a needle portion and a signal generator portion.

The needle portion comprises a needle hub 70 with a needle 71 extending therefrom. The needle hub 70 has a threaded annular flange 72 at the end opposite from the needle 71. The thread is a male thread 74. The needle hub has an inner lumen 75 which is smoothly tapered to the needle connection point 76. Within the needle hub 70 there is also an information encoding component 78 such as an electrical resistor, capacitor and/or programmable device.

The signal generator portion comprises a body 80 with a rear housing 84 enclosing a speaker 82 and a locking ring 86. The locking ring 86 has a female thread 88. The body 80 has an inner lumen 90 which is smoothly tapered from the speaker output cone 92 to the beginning of the inner lumen 75 of the needle hub 70. Also in the body is an interrogating means 94 which when the needle hub is connected to the body engages the information encoding component 78. Wires 91 extend to the speaker 82 and wires 95 extend to the interrogating means 94.

A suitable alignment groove 79 in the needle hub and projection 93 on the body ensures correct mating of the signal generator portion to the needle hub. The locking ring 86 is freely movable on the body 80 so that once the alignment groove 79 in the needle hub and projection 93 on the body have been engaged the male thread 74 can engage the female thread 88 to securely connect the two portions and ensure correct alignment of the respective inner lumens 75 and 90 and correct connection of the interrogation means 94 with the information encoding device 78.

What is claimed is:

1. A medical apparatus including a probe, the probe having a characteristic which is useful to assist with the positioning of the probe in a human or animal body, and an information encoding component on the probe, a selected value of the information encoding component corresponding to the characteristic of the probe, wherein the characteristic is a resonant frequency of the probe which enhances the visibility of the tip of the probe to Doppler ultrasound imaging.

2. A medical apparatus as in claim 1, wherein the probe is a hollow probe.

3. A medical apparatus as in claim 1, wherein the information encoding component is selected from the group which comprises an electrical resistor, a capacitor and a programmable device.

4. A medical apparatus as in claim 1, wherein the probe comprises a hollow tube and a connector at one end thereof and the information encoding component is associated with the connector.

5. A medical apparatus including a probe, the probe having a characteristic which is useful to assist with the positioning of the probe in a human or animal body, and an information encoding component on the probe, a selected value of the information encoding component corresponding to the characteristic of the probe, wherein the probe is a dual lumen needle comprising an inner needle and an outer needle.

6. A medical apparatus as in claim 5, wherein the distal end of the inner needle has a closed end and a side hole.

7. A medical apparatus including a probe, the probe having a characteristic which is useful to assist with the positioning of the probe in a human or animal body, and an information encoding component on the probe, a selected value of the information encoding component corresponding to the characteristic of the probe, and a signal generating device for the probe and an interrogating component associated with the signal generating device to interrogate the information encoding component on the probe, wherein the signal generating device is adapted to provide an acoustic signal.

8. A medical apparatus comprising a hollow probe, a signal generating device and a connecting tube between the hollow probe and the signal generating device, a first connector between the signal generating device and the connecting tube, the first connector including a first portion associated with the signal generating device and a second portion associated with the connecting tube, an information encoding component associated with the second portion, fixedly associated with the hollow probe, and corresponding to a characteristic of the hollow probe and an interrogating means associated with the first portion wherein when the first and second portions of the first connector are connected, the interrogating means engages and is able to interrogate the information encoding component.

9. A medical apparatus as in claim 8, wherein the information encoding component is selected from the group which comprises an electrical resistor, a capacitor and a programmable device.

10. A medical apparatus as in claim 8, wherein the first connector provides a smooth air conduit between the signal generating device and the bore of the connecting tube.

11. A medical apparatus as in claim 8, further comprising a second connector between the connecting tube and the hollow probe.

12. A medical apparatus as in claim 8, wherein the hollow probe is a dual lumen needle comprising an inner needle and an outer needle.

13. A medical apparatus as in claim 12, wherein the second connector provides a smooth air conduit between the bore of the connecting tube and the bore of the inner needle.

14. A medical apparatus as in claim 13, wherein the second connector includes means to enable disconnection of the coupling tube from the outer needle and removal of the coupling tube and inner needle while leaving the outer tube insitu.

15. A medical apparatus as in claim 13, wherein the distal end of the inner needle has a closed end and a side hole.

16. A medical apparatus as in claim 13, wherein the signal generating device is adapted to provide an acoustic signal.

17. A medical apparatus as in claim 13 further including an electronic control circuit adapted to interrogate the information encoding component and to adjust the frequency of the signal provided by the signal generating means.

18. A medical apparatus comprising a hollow probe having an inner needle and an outer needle, a signal generating device and a connector between the signal generating and the hollow probe, the connector comprising a first portion associated with the signal generating device and a second portion associated with the hollow probe, an information encoding component associated with the second portion, fixedly associated with the hollow probe and corresponding to a characteristic of the hollow probe and interrogating means associated with the first portion wherein when the first and second portions of the connector are connected, the interrogation means engages the information encoding component, and wherein the connector includes is adapted to enable disconnection of the signal generating device from the outer needle and removal of the inner needle while leaving the outer needle insitu.

19. A medical apparatus as in claim 18, wherein the information encoding component is selected from the group which comprises an electrical resistor, a capacitor and a programmable device.

20. A medical apparatus as in claim 18, wherein the connector provides a smooth air conduit between the signal generating device and the bore of the hollow probe.

21. A medical apparatus comprising a signal generating device in a housing and a hollow probe, the hollow probe having a hub at one end thereof and an aperture through the hub providing a fluid passage into the hollow probe, a connection assembly between the housing and the hub, a signal port in the housing extending from the signal generating device to the aperture in the hub, characterized by a smooth fluid conduit extending from the signal port through the aperture to the hollow probe, the hub having an information encoding component thereon and corresponding to a characteristic of the hollow probe and the housing having an interrogating component wherein the connection of the hub to the housing by means of the connection assembly enables the interrogating component to engage the information encoding component.

22. A medical apparatus as in claim 21, wherein the signal generating device is adapted to provide an acoustic signal.

23. A medical apparatus as in claim 21, wherein the aperture is tapered to connect with a Luer fitting.

24. A medical apparatus as in claim 21, wherein the hollow probe further comprises a dual lumen needle comprising an inner needle and an outer needle.

25. A medical apparatus as in claim 21 wherein the information encoding component is selected from the group which comprises an electrical resistor, a capacitor and a programmable device.

26. A medical apparatus comprising a hollow probe and a signal generating device and a connection assembly between the signal generating device and the hollow probe, the hollow probe having a first bore and the signal generating device having a signal port having a second bore, the connection assembly including a first portion associated with the signal generating device and a second portion associated with the hollow probe and a hub associated with either the first portion or the second portion, the hub including an aperture providing a smooth fluid conduit between the first bore and the second bore, the hollow probe having an information encoding component thereon and corresponding to a characteristic of the hollow probe and the signal generating device having an interrogating component wherein connection of the hollow probe to the signal generating device by means of the connection assembly enables the interrogating means to engage the information encoding component.

27. A medical apparatus as in claim 26, wherein the aperture is of frustoconical shape having a diameter at one end equivalent to the diameter of the first bore and the diameter at its other end equivalent to the diameter of the second bore.

28. A medical apparatus as in claim 26, wherein the aperture is tapered to connect with a Luer fitting.

29. A medical apparatus as in claim 26, further including the hollow probe further comprising a dual lumen needle, comprising an inner needle and an outer needle.

30. A medical apparatus as in claim 26, wherein the information encoding components selected from the group which comprises an electrical resistor, a capacitor, and a programmable device.

31. A connection between a signal generating device and a hollow probe, the connection providing a smooth air conduit from the signal generating device to the hollow probe, the connection including an information encoding component fixedly associated with the probe and corresponding to a characteristic of the hollow probe and an interrogating component associated with the signal generating device and making the connection enables the interrogating component to engage the information encoding component.

32. A connection as in claim 31, wherein the connection includes a tapered portion associated with the hollow probe to enable connection thereto of a Luer fitting.

33. A connection as in claim 31, wherein the information encoding component is selected from the group which comprises an electrical resistor, a capacitor, and a programmable device.

* * * * *